(12) United States Patent
Chang

(10) Patent No.: US 10,524,781 B2
(45) Date of Patent: Jan. 7, 2020

(54) NEEDLE INSTRUMENT FOR EYE-BAG RELOCATING OPERATION

(71) Applicant: Cheol Ho Chang, Seoul (KR)

(72) Inventor: Cheol Ho Chang, Seoul (KR)

( * ) Notice: Subject to any disclaimer, the term of this patent is extended or adjusted under 35 U.S.C. 154(b) by 0 days.

(21) Appl. No.: 16/082,423

(22) PCT Filed: Apr. 4, 2018

(86) PCT No.: PCT/KR2018/003982
§ 371 (c)(1),
(2) Date: Sep. 5, 2018

(87) PCT Pub. No.: WO2018/208014
PCT Pub. Date: Nov. 15, 2018

(65) Prior Publication Data
US 2019/0307446 A1    Oct. 10, 2019

(30) Foreign Application Priority Data

May 12, 2017   (KR) .................. 10-2017-0059275

(51) Int. Cl.
*A61B 17/04* (2006.01)
*A61B 17/06* (2006.01)
*A61B 17/00* (2006.01)

(52) U.S. Cl.
CPC .... *A61B 17/0485* (2013.01); *A61B 17/06066* (2013.01); *A61B 2017/00747* (2013.01); *A61B 2017/00792* (2013.01)

(58) Field of Classification Search
CPC .......... A61B 17/0485; A61B 17/06066; A61B 17/06; A61B 2017/06085; A61B 2017/0609
See application file for complete search history.

(56) References Cited

U.S. PATENT DOCUMENTS

| 4,327,655 A | * | 5/1982 | Addy | ................... D05B 81/00 112/222 |
| 5,569,301 A | * | 10/1996 | Granger | ............. A61B 17/0469 606/223 |
| 5,693,071 A | * | 12/1997 | Gorecki | ............. A61B 17/0469 606/222 |

(Continued)

FOREIGN PATENT DOCUMENTS

| JP | 2000-342593 A | 12/2000 |
| JP | 2016-195777 A | 11/2016 |

(Continued)

*Primary Examiner* — Phong Son H Dang
(74) *Attorney, Agent, or Firm* — Novick, Kim & Lee, PLLC; Jae Youn Kim

(57) ABSTRACT

The present invention relates to a needle instrument for an eye-bag relocating operation. The needle instrument includes a body unit having a rectangular cross-section and grabbed by a needle holder during the operation; a needle unit having one needle side and the other needle side on both sides of the body unit to be tapered and having round tips, wherein one needle side is formed to be duller than the other needle side; and a thread pressing and coupling unit provided on one end of the body unit and formed at a position that corresponds to ⅕ to ⅙ of an entire length from an end of the needle instrument and is spaced apart from the end of the body unit by 0.5 to 1 mm.

5 Claims, 15 Drawing Sheets

(56) References Cited

U.S. PATENT DOCUMENTS

| | | | | |
|---|---|---|---|---|
| 5,865,836 A * | 2/1999 | Miller | A61B 17/06 | 606/222 |
| 5,891,164 A * | 4/1999 | Dabir | A61B 17/06066 | 606/222 |
| 6,056,771 A * | 5/2000 | Proto | A61B 17/0469 | 606/222 |
| 6,129,741 A * | 10/2000 | Wurster | A61B 17/0469 | 289/16 |
| 6,159,233 A * | 12/2000 | Matsuzawa | A61B 17/06066 | 606/223 |
| 6,322,581 B1 * | 11/2001 | Fukuda | A61B 17/06066 | 606/222 |
| 7,063,716 B2 | 6/2006 | Cunningham | A61B 17/06066 | 606/222 |
| 8,512,373 B2 * | 8/2013 | Gilson | A61B 17/06066 | 606/224 |
| 8,597,326 B2 * | 12/2013 | Matsutani | A61B 17/06066 | 606/223 |
| 8,778,102 B2 * | 7/2014 | Maurer | B23K 26/389 | 148/668 |
| 9,033,999 B2 * | 5/2015 | Mueller | A61B 17/0401 | 606/139 |
| 9,408,601 B2 * | 8/2016 | Nakayama | B24B 19/16 | |
| 9,675,340 B2 * | 6/2017 | Sniffin | A61B 17/06066 | |
| 2005/0256535 A1 * | 11/2005 | Capurro | A61B 17/06004 | 606/185 |
| 2006/0020324 A1 * | 1/2006 | Schmid | A61F 2/856 | 623/1.16 |
| 2006/0047309 A1 * | 3/2006 | Cichocki, Jr. | A61B 17/06066 | 606/222 |
| 2007/0167955 A1 * | 7/2007 | Arnault De La Menardiere | A61F 2/954 | 606/108 |
| 2007/0219586 A1 * | 9/2007 | Mahadevan | A61B 17/06066 | 606/223 |
| 2008/0287956 A1 * | 11/2008 | Smith | A61B 17/06066 | 606/99 |
| 2009/0312720 A1 * | 12/2009 | Maurer | B23K 26/389 | 604/273 |
| 2010/0023053 A1 * | 1/2010 | Akutsu | A61B 17/06066 | 606/223 |
| 2010/0069956 A1 * | 3/2010 | Matsutani | A61B 17/06066 | 606/222 |
| 2010/0100125 A1 * | 4/2010 | Mahadevan | A61B 17/06066 | 606/223 |
| 2011/0112575 A1 * | 5/2011 | Tochimura | A61B 17/06066 | 606/222 |
| 2011/0282385 A1 * | 11/2011 | Gilson | A61B 17/06066 | 606/224 |
| 2011/0301642 A1 * | 12/2011 | White | A61B 17/06066 | 606/223 |
| 2012/0158049 A1 * | 6/2012 | Kato | A61B 17/06066 | 606/223 |
| 2014/0005719 A1 * | 1/2014 | Uetake | A61B 17/06066 | 606/223 |
| 2015/0142018 A1 * | 5/2015 | Sniffin | A61B 17/06066 | 606/144 |
| 2018/0116660 A1 * | 5/2018 | Chang | A61B 17/06066 | |

FOREIGN PATENT DOCUMENTS

| | | |
|---|---|---|
| KR | 10-1998-0072154 A | 10/1998 |
| KR | 10-0334927 B1 | 5/2002 |
| KR | 10-2006-0059933 A | 6/2006 |
| KR | 10-2013-0097415 A | 9/2013 |
| KR | 10-2015-0107292 A | 9/2015 |

* cited by examiner

NEEDLE INSTRUMENT FOR EYE-BAG RELOCATING OPERATION

TECHNICAL FIELD

The present invention relates to a surgical needle instrument. More particularly, the invention relates to a needle instrument for an eye-bag relocating operation, which spreads a part of an eye bag according to the distribution of the eye bag and then relocates the eye bag in a sunken lacrimal groove under the eye.

BACKGROUND ART

Generally, as an orbital septum surrounding the fat of the lower eyelid becomes weak with age, the fat in the orbital septum swells and sags under the eye. Consequently, shadow may be formed along the skeleton adjacent to the nose and the pigmentation of skin may be caused, thus leading to dark circles that make a region under the eye look dark. Further, as the skin sags and acquires wrinkles, a person's face may look tired. The cause why fat is accumulated under the eye is known as a kind of aging process. The accumulation of the fat may be sometimes accompanied by diseases such as hyperthyroidism, renal failure, rhinitis and asthma.

Once a person gets the eye bag, it is difficult to remove the eye bag through massage or meridian massage, and the eye bag is not naturally restored to its original shape. Therefore, it is necessary to surgically remove the eye bag in plastic surgery. A surgical procedure for removing the eye bag while reducing wrinkles under the eye is referred to as lower eyelid surgery. This procedure is problematic in that a region under the eyebrow is incised, so that a patient may often get a bruise on his or her surgical site, and under-eye fat may disappear, and thereby the face may look flat and complications such as ectropion and involution may occur.

Recently, an eye-bag relocating operation is carried out instead of completely removing the eye bag. This operation removes some unnecessary fat and relocates some fat in a sunken lacrimal groove under the eye according to the distribution of the eye bag, thus avoiding the dark circle and minimizing a depression under the eye.

As the related art concerning the eye-bag relocating operation, there have been proposed a skin incision procedure where the skin under the eye is incised and a conjunctiva incision procedure where the conjunctiva inside the eye is incised. The conjunctiva incision procedure is preferred because a scar is not visible from the outside, as long as the skin does not sag excessively.

Such a conjunctiva incision procedure may adopt an external fixing method and an internal fixing method, as a method for relocating the swelling eye bag in the lacrimal groove and fixing the relocated eye bag.

The external fixing method is a method where the eye bag is tied with thread, the thread is pulled out through a needle and then is taped and fixed, and this state is kept for about one week, thus inducing the natural adhesion of shifted fat. Meanwhile, the internal fixing method is a method where the eye bag is internally fixed under an excoriated lacrimal groove with thread.

The external fixing method is advantageous in that it is easy to perform the procedure through the conjunctiva, and it is possible to sufficiently move the eye bag to a desired position in an excoriated space. However, the external fixing method is problematic in that taping is required, a patient should visit a hospital within one week after the surgical procedure so as to remove the thread, and a skin trouble or an inflammation may be caused by the thread passing through the skin and the taping.

The internal fixing method is advantageous in that this method is more robust than the external fixing method, there is little recurrence, and it is unnecessary for a patient to visit a hospital so as to remove the taping and the thread. However, the internal fixing method is problematic in that a visual field is limited when the conjunctiva is incised, so that it is complicated to perform the internal fixing method, an incision line should be formed long to secure a clear view, so that the conjunctiva may be badly scarred and adhered, and the eye bag may not sufficiently moved down to the lacrimal groove due to a small surgical space, and consequently a satisfactory effect of treatment may not be obtained.

Further, as the related art, Korean Patent Laid-Open Publication No. 10-2015-0107292 discloses a needle for plastic surgery with suture thread.

DISCLOSURE

Technical Problem

Accordingly, the present invention has been made keeping in mind the above problems occurring in the related art, and is intended to provide a needle instrument for an eye-bag relocating operation, which minimizes the incision of the conjunctiva inside the eye, reduces a scar in conjunctiva, facilitates an internal fixing procedure, and allows an eye bag to be relocated at a sufficient lower position in a lacrimal groove, so that the effect of treatment is improved and robust internal fixing is achieved, and consequently it is unnecessary to relocate the eye bag again, and a damage to skin and a dimple phenomenon where a skin surface is rugged after a surgical procedure may be prevented.

Further, the present invention is intended to provide a needle instrument for an eye-bag relocating operation, which may be firmly grabbed by a needle holder and in which the strength of a needle is maintained, so that an operator does not miss the needle and the needle is not broken during a surgical procedure, thus increasing both the stability of the procedure and the durability of the needle.

Furthermore, the present invention is intended to provide a needle instrument for an eye-bag relocating operation, which avoids a patent discomfort resulting from taping, obviates the necessity for a patient to visit a hospital for the purpose of removing taping and thread, and prevents a skin trouble or an inflammation from being caused by the thread passing through the skin and the taping.

Technical Solution

In order to accomplish the above objects, the present invention provides a needle instrument for an eye-bag relocating operation, which is used to fix an eye bag relocated at a lower position in a lacrimal groove during the eye-bag relocating operation and has an arc shape, the needle instrument including a body unit having a rectangular cross-section, and grabbed by a needle holder during the operation; a needle unit having one needle side and the other needle side on both sides of the body unit to be tapered, and having round tips, wherein one needle side is formed to be duller than the other needle side; and a thread pressing and coupling unit provided on one end of the body unit, and formed at a position that corresponds to $\frac{1}{5}$ to $\frac{1}{6}$ of an entire length from an end of the needle instrument and is spaced apart from the end of the body unit by 0.5 to 1 mm, wherein, after a through hole is formed through the thread pressing and coupling unit and thread is connected to the through hole, both sides of the body unit are pressed by a press machine to attach the thread thereto.

Further, the present invention provides a needle instrument for an eye-bag relocating operation, which is used to fix an eye bag relocated at a lower position in a lacrimal groove during the eye-bag relocating operation and has an arc shape, the needle instrument including a body unit having a rectangular cross-section, and grabbed by a needle holder during the operation; a needle unit having one needle side and the other needle side on both sides of the body unit to be tapered, wherein one needle side has a round tip and the other needle side has a tip that is cut in a triangular shape; and a thread pressing and coupling unit provided on one end of the body unit, and formed at a position that corresponds to ⅕ to ⅙ of an entire length from an end of the needle instrument and is spaced apart from the end of the body unit by 0.5 to 1 mm, wherein, after a through hole is formed through the thread pressing and coupling unit and thread is connected to the through hole, both sides of the body unit are pressed by a press machine to attach the thread thereto.

Advantageous Effects

The present invention provides a needle instrument for an eye-bag relocating operation, which minimizes the incision of the conjunctiva inside the eye, reduces a scar in conjunctiva, facilitates an internal fixing procedure, and allows an eye bag to be relocated at a sufficient lower position in a lacrimal groove, so that the effect of treatment is improved and robust internal fixing is achieved, and consequently it is unnecessary to relocate the eye bag again, and a damage to skin and a dimple phenomenon where a skin surface is rugged after a surgical procedure may be prevented.

Further, the present invention provides a needle instrument for an eye-bag relocating operation, which may be firmly grabbed by a needle holder and in which the strength of a needle is maintained, so that an operator does not miss the needle and the needle is not broken during a surgical procedure, thus increasing both the stability of the procedure and the durability of the needle.

Furthermore, the present invention provides a needle instrument for an eye-bag relocating operation, which avoids a patent discomfort resulting from taping, obviates the necessity for a patient to visit a hospital for the purpose of removing taping and thread, and prevents a skin trouble or an inflammation from being caused by the thread passing through the skin and the taping.

BRIEF DESCRIPTION OF THE DRAWINGS

The accompanying drawings are intended to illustrate the preferred embodiments of the invention, and aid in understanding the technical spirit of the invention when reading the following description. It is to be interpreted that the invention is not limited to embodiments shown in the drawings.

BEST MODE FOR THE INVENTION

Figure 1:
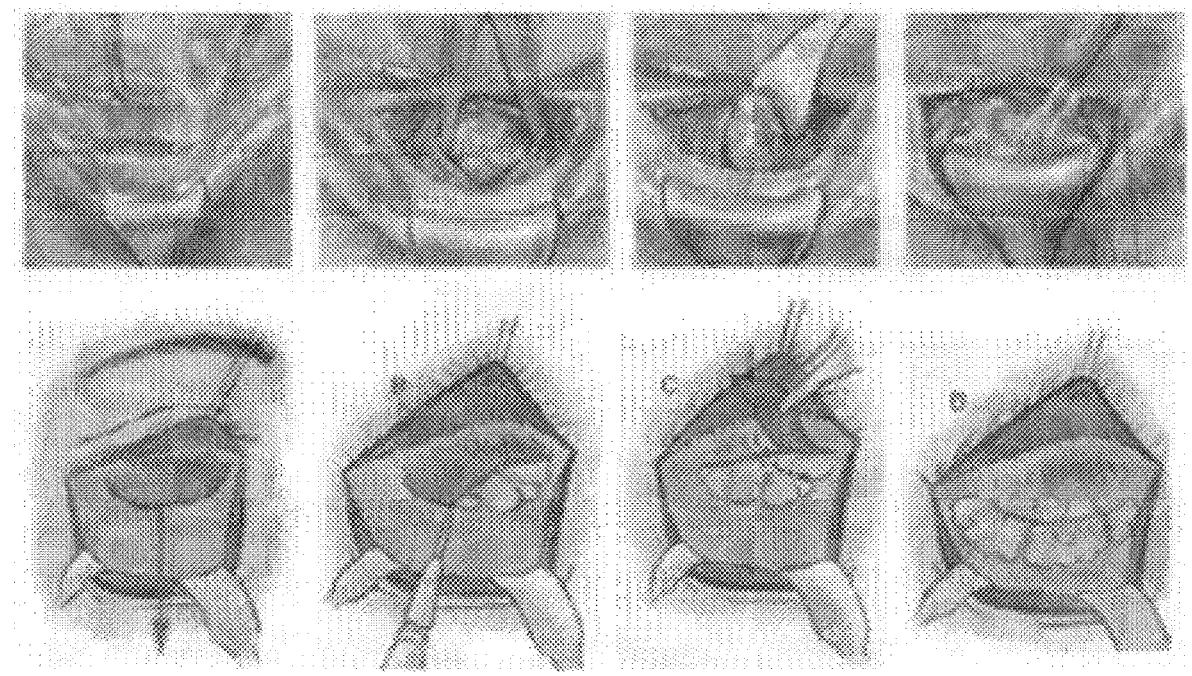
FIG. 1 is a view illustrating a surgical procedure of relocating an eye bag according to a conventional internal incision method.

Hereinafter, a needle instrument for an eye-bag relocating operation according to an embodiment of the present invention will be described in more detail with reference to the accompanying drawings.

The needle instrument 10 for the eye-bag relocating operation according to the present invention is utilized to fix the eye bag when a part of the eye bag is spread according to the distribution of the eye bag and then relocated in a sunken lacrimal groove under the eye. The needle instrument has the shape of arc that corresponds to ⅜ of a circle, and includes a body unit 100, a needle unit 200, and a thread pressing and coupling unit 300.

The body unit 100 is a part grabbed by a needle holder that is a tool for holding a needle during surgery. Preferably, the body unit has a cross-section of a rectangle that is slightly elongated in a vertical direction.

Since the body unit 100 has a rectangular cross-section, the needle is more easily and strongly grabbed as compared to a circular cross-section. Thus, the risk of missing the needle instrument is reduced, so that the stability of a procedure is increased. Although a through hole is bored through the thread pressing and coupling unit 300, it is possible to maintain the durability of the needle. Further, a pressing operation is easily performed by a press machine.

The needle unit 200 has one needle side 210 and the other needle side 220 that are provided on both sides of the body unit 100 to be tapered towards ends, thus serving as needles. Thus, the needle unit is penetrated into and then pulled out from the eye bag or the skin. Unlike the related art wherein the needle is formed only on one end, the needles are formed on both ends. Such a structure facilitates an internal fixing procedure to the eye bag even within a limited visual field during internal approach through the conjunctiva. Further, it is possible to minimize the conjunctiva incision, to increase reliability when the eye bag is fixed at a lower position, and to offer a higher fixing force.

Figure 2A:
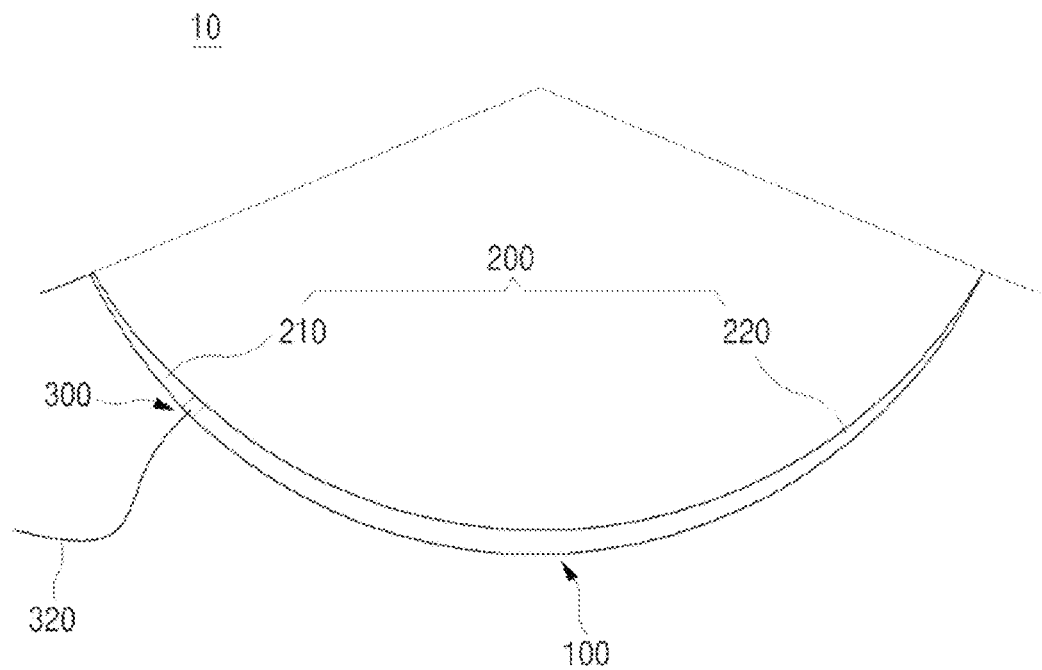
FIG. 2A is a front view of a needle instrument according to an embodiment of the present invention.
Figure 2B:
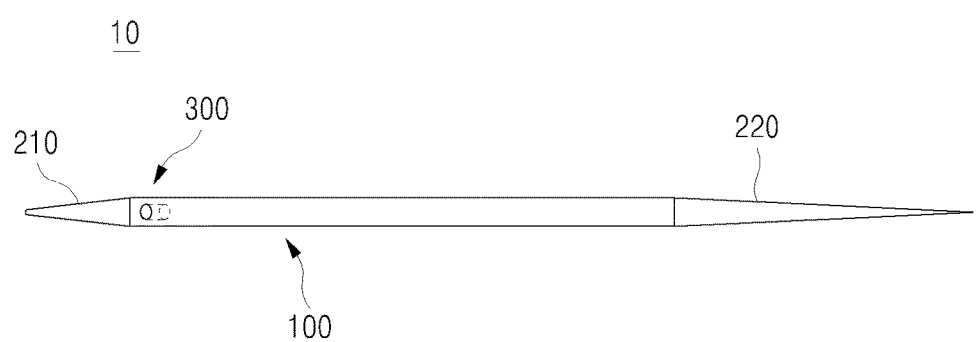
FIG. 2B is a plan view of the needle instrument.
Figure 2C:
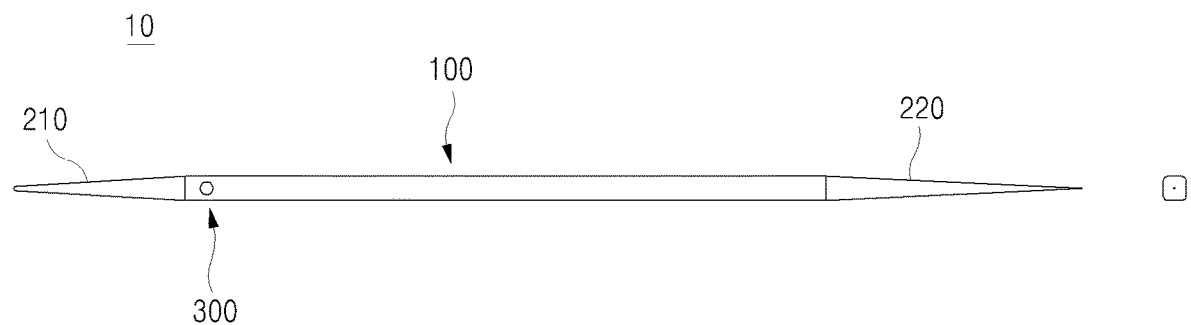
FIG. 2C is a development view of an arc-shaped needle instrument.

According to the embodiment, referring to FIGS. 2A to 2C, ends of one needle side 210 and the other needle side 220 are formed in the shape of round tips. The round tip of one needle side 210 is formed to be duller than the round tip of the other needle side 220.

Since the round tip of the other needle side 220 that should penetrate through the skin 6 is formed to be sharper than one needle side 210, this allows the needle instrument 10 to more easily pass through the skin. Further, since the round tip of one needle side 210 penetrating into subcutaneous tissue 7 is formed to be duller than the other needle side 220, this may minimize damage to blood vessels, nerves and the like in the subcutaneous tissue 7 when the needle instrument 10 is rotated in the subcutaneous tissue 7 or is moved out of the subcutaneous tissue 7, in addition to maximally protecting an eyeball 8 adjacent to the conjunctiva 3.

The thread pressing and coupling unit 300 is formed on only one end of the body unit 100 but is not formed on the other end thereof, with thread 320 being coupled thereto. For example, as illustrated in FIGS. 2A to 2C, the through hole is formed through the thread pressing and coupling unit 300 and the thread is inserted into the through hole. In this state, both sides of the body unit 100 are pressed by the press machine and the thread is attached to the thread pressing and coupling unit 300, so that it is manufactured in a thread attachment type and thereby an operator may use it in a convenient manner. The thread attachment type does not press the thread pressing and coupling unit 300 but presses both sides of the body unit 100 by the press machine. The reason is as follows: in the case of pressing only the thread pressing and coupling unit 300 having the through hole, only the thread pressing and coupling unit 300 is reduced in thickness and the strength and durability of the needle instrument 10 are reduced, so that the needle instrument may be broken. When comparing the thread attachment type with the thread connection type, the body unit 100 of the thread attachment type has a square cross-section.

Preferably, the thread pressing and coupling unit 300 is formed as close as possible to one needle side 210. For example, the thread pressing and coupling unit may be formed at a position that corresponds to ⅕ to ⅙ of the entire arc length from an end of the needle instrument 10. In other words, this is spaced apart from a boundary surface between one needle side 210 and the body unit 100 by 0.5 to 1 mm to be located in the body unit 100. The reason why the thread pressing and coupling unit is located as such is as follows: when the thread pressing and coupling unit 300 is formed on one needle side 210, the strength of the needle instrument is reduced, so that the needle may be broken during the surgical procedure. Further, as the thread pressing and coupling unit 300 approaches the center of the body unit 100, dimples, that is, a phenomenon where the surface of the skin becomes rugged may occur after the surgical procedure, in the case where the thread pressing and coupling unit 300 comes near to the skin 6 or passes through the skin when the needle instrument 10 is pulled towards the skin 6 such that the other needle side 220 is not visible from the conjunctiva 3.

Figure 3A:
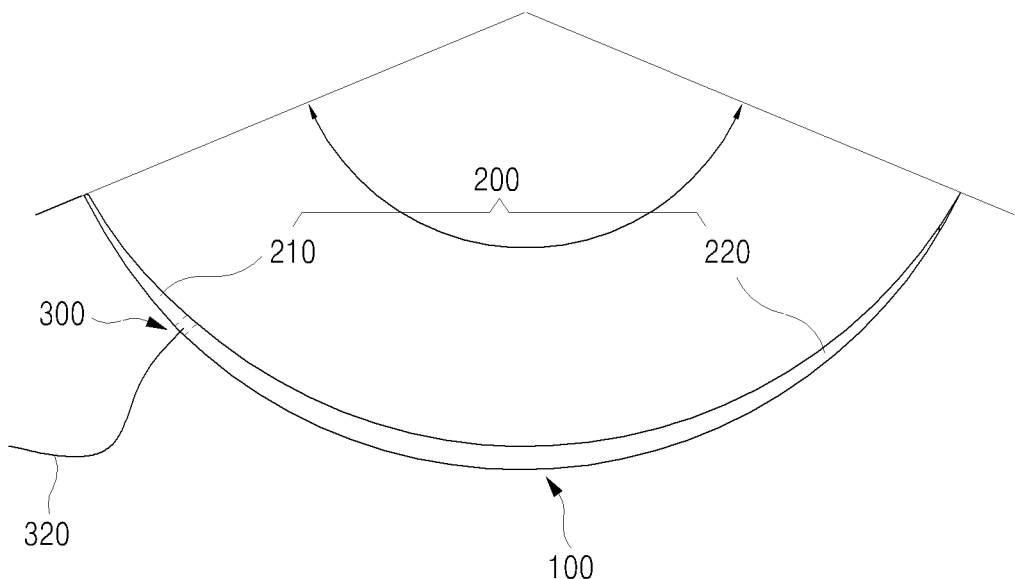
FIG. 3A is a front view of a needle instrument according to an embodiment of the present invention.
Figure 3B:
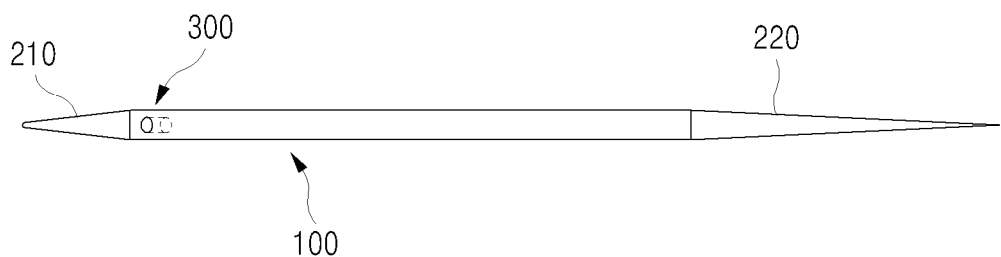
FIG. 3B is a plan view of the needle instrument.
Figure 3C:
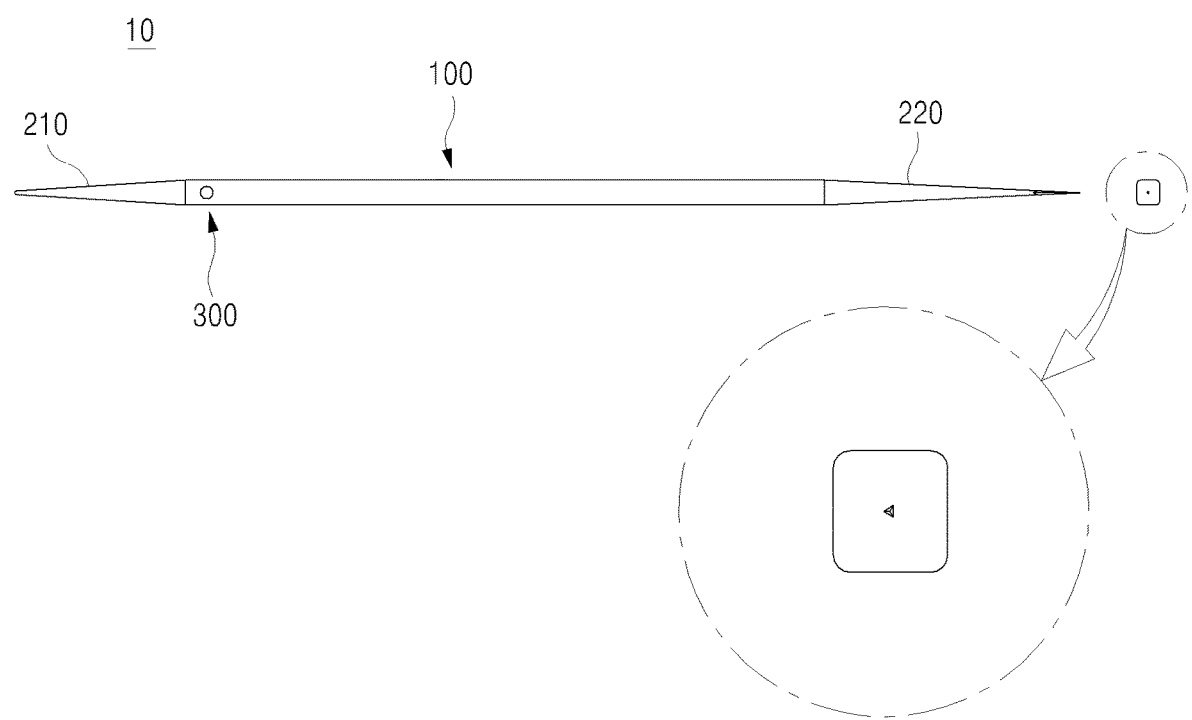
FIG. 3C is a development view of an arc-shaped needle instrument.

Referring to FIGS. 3A to 3C, in the needle unit 200, the end of one needle side 210 is formed to have a round tip and the other needle side 220 generally has a round shape. However, in order to make it easier to pass through the skin, the end of the other need side has a tip that is cut in a triangular shape. The end of the other needle side 220 has a length ranging from 1 to 2 mm from an end point.

The triangular tip of the end of the other needle side 220 that should pass through the skin 6 allows the needle instrument 10 to easily pass through the skin, while the dull round tip of one needle side 210 penetrated into the subcutaneous tissue 7 minimizes damage to blood vessels, nerves and the like in the subcutaneous tissue 7 when the needle instrument 10 is rotated in the subcutaneous tissue 7 or is moved out of the subcutaneous tissue 7, in addition to maximally protecting the eyeball 8 adjacent to the conjunctiva 3.

For example, as illustrated in FIGS. 3A to 3C, the through hole is formed through the thread pressing and coupling unit 300 and the thread is inserted into the through hole. In this state, both sides of the body unit 100 are pressed by the press machine and the thread is attached to the thread pressing and coupling unit 300, so that it is manufactured in the thread attachment type and thereby an operator may use it in a convenient manner. The thread attachment type does not press the thread pressing and coupling unit 300 but presses both sides of the body unit 100 by the press machine. The reason is as follows: in the case of pressing only the thread pressing and coupling unit 300 having the through hole, only the thread pressing and coupling unit 300 is reduced in thickness and the strength and durability of the needle instrument 10 are reduced, so that the needle instrument may be broken.

Hereinafter, the surgical procedure using the needle instrument 10 according to the present invention will be described with reference to FIGS. 4A to 5F.

Figure 4A:
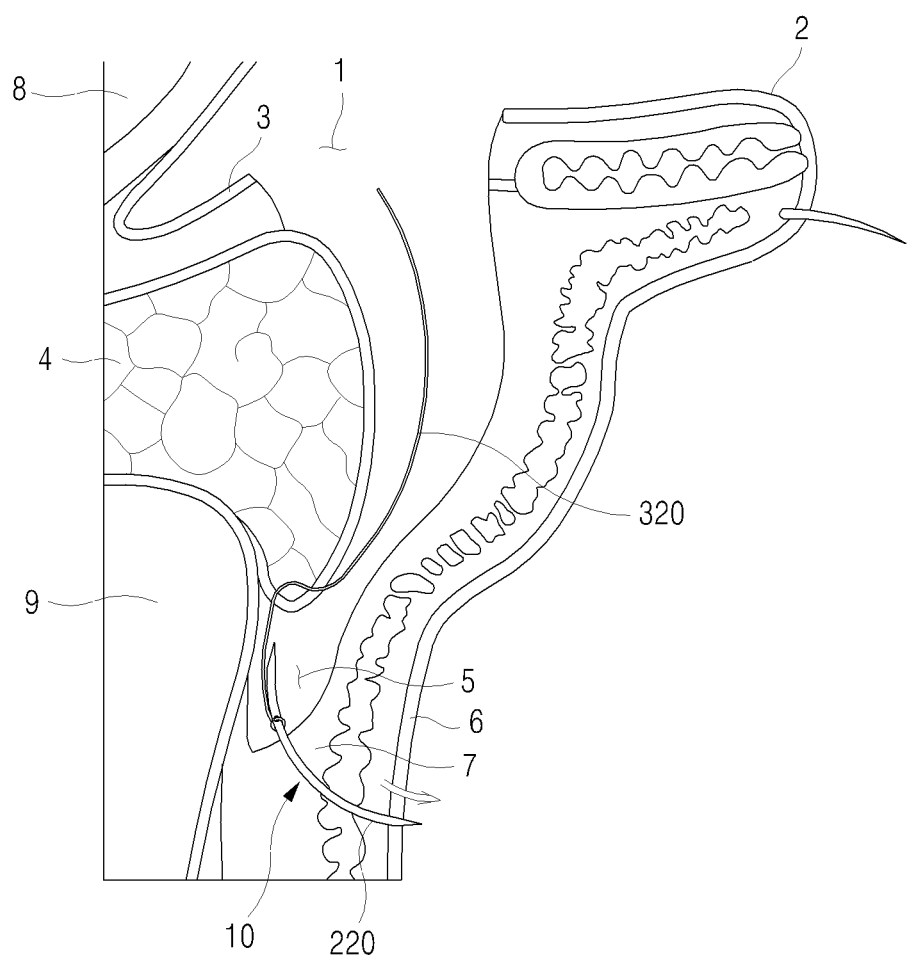
FIGS. 4A to 4D are views illustrating a surgical procedure of relocating an eye bag using the needle instrument according to the embodiment of the present invention.

The conjunctiva 3 inside the lower eyelid 2 is incised to the minimum by an electric knife or laser. While the needle instrument 10 of the present invention is inserted down through the incised conjunctiva 3 as illustrated in FIG. 4A, the needle instrument 10 is connected to the eye bag 4 with the thread. If the needle instrument 10 reaches the lacrimal groove 5 under an eye socket 1, the other needle side 220 of the needle instrument passes through the subcutaneous tissue 7 and the skin 6 outside the lacrimal groove 5 to be exposed to an outside. One needle side 210 is penetrated into the subcutaneous tissue 7 together with the thread 320.

Figure 4B:
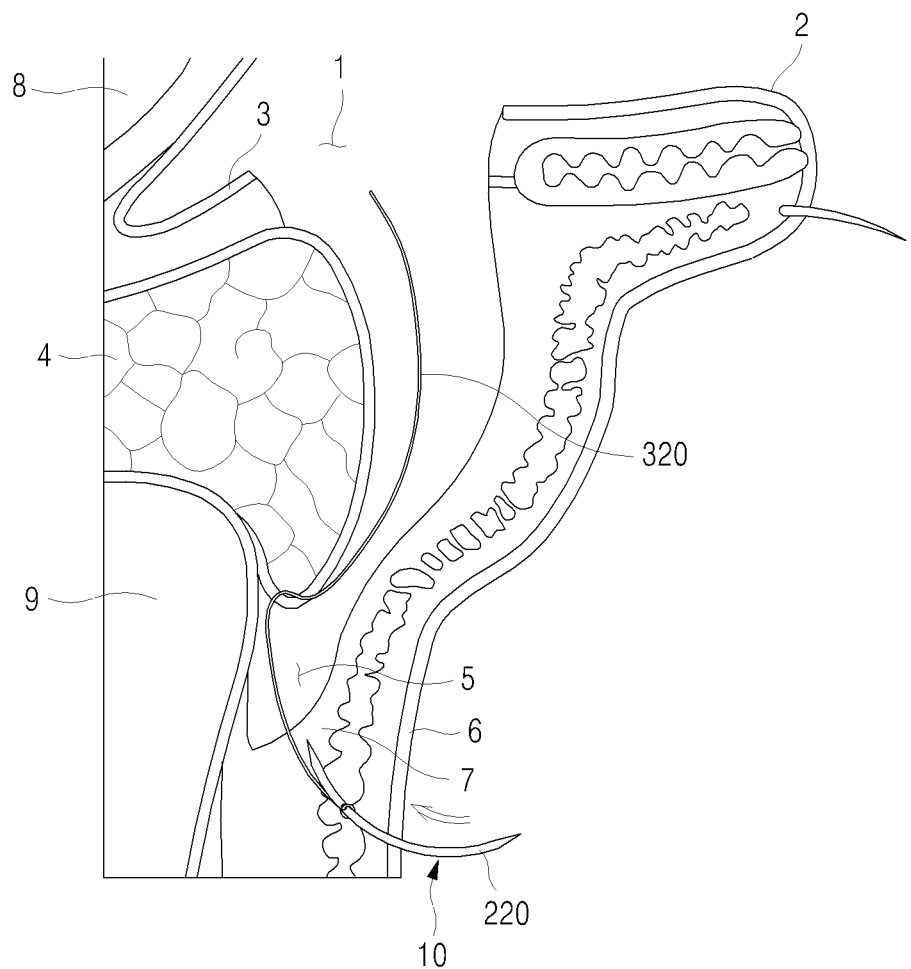
Figure 4C:
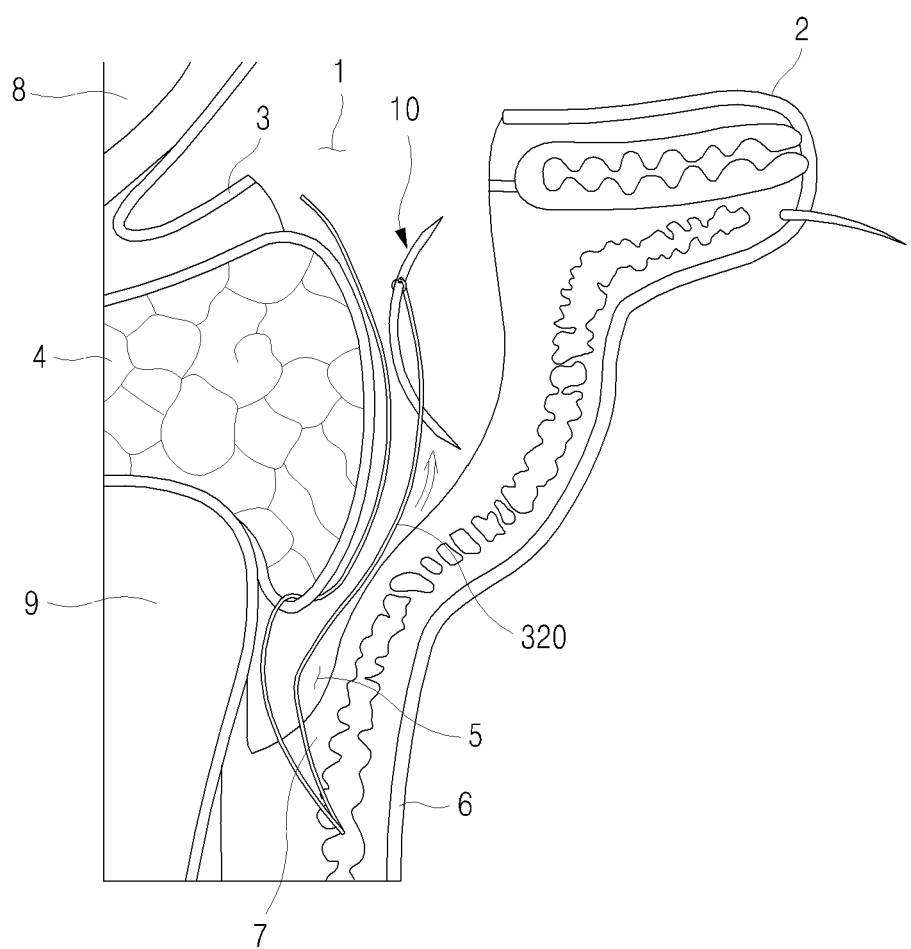
Figure 4D:
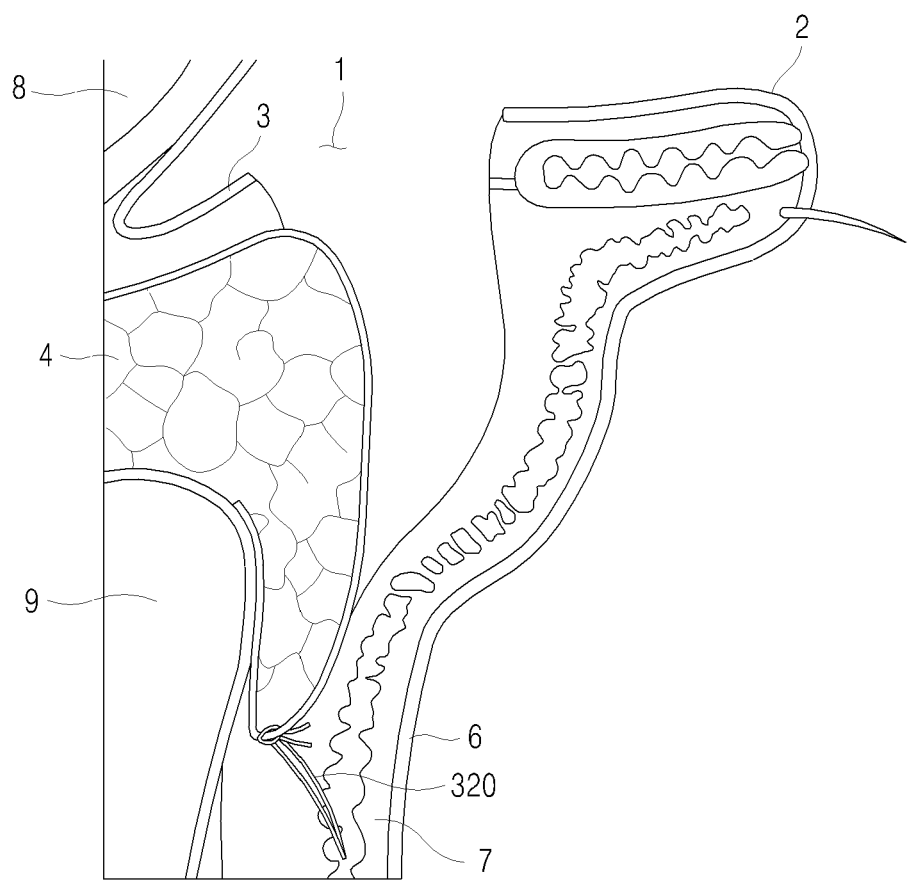

If the needle instrument 10 is removed from the subcutaneous tissue 7 starting from one needle side 210 and the needle instrument 10 is pulled up as illustrated in FIG. 4C after the needle instrument 10 is rotated or moved from the outside as illustrated in FIG. 4B, the thread 320 is caught by the subcutaneous tissue 7 as illustrated in FIG. 4D. This is possible because the body unit 100 is formed in the arc shape and the needle unit 200 has sharp ends.

Figure 5A:
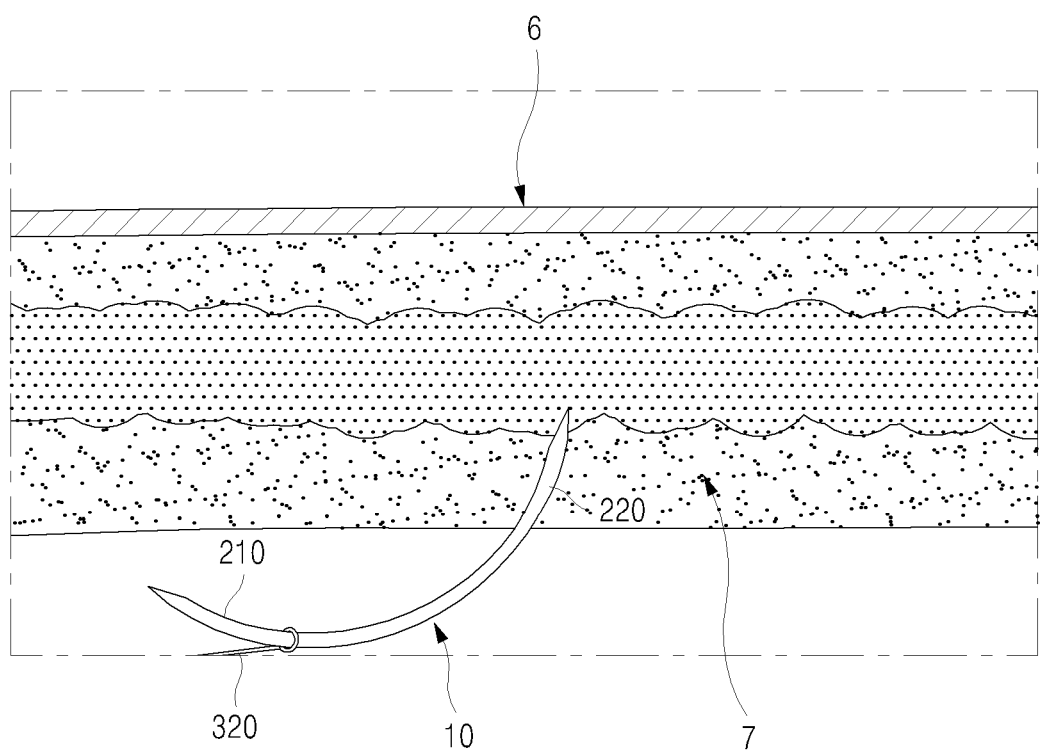
FIGS. 5A to 5F are views illustrating the details of a procedure of fixing the thread of the needle instrument according to the embodiment of the present invention to the skin.
Figure 5B:
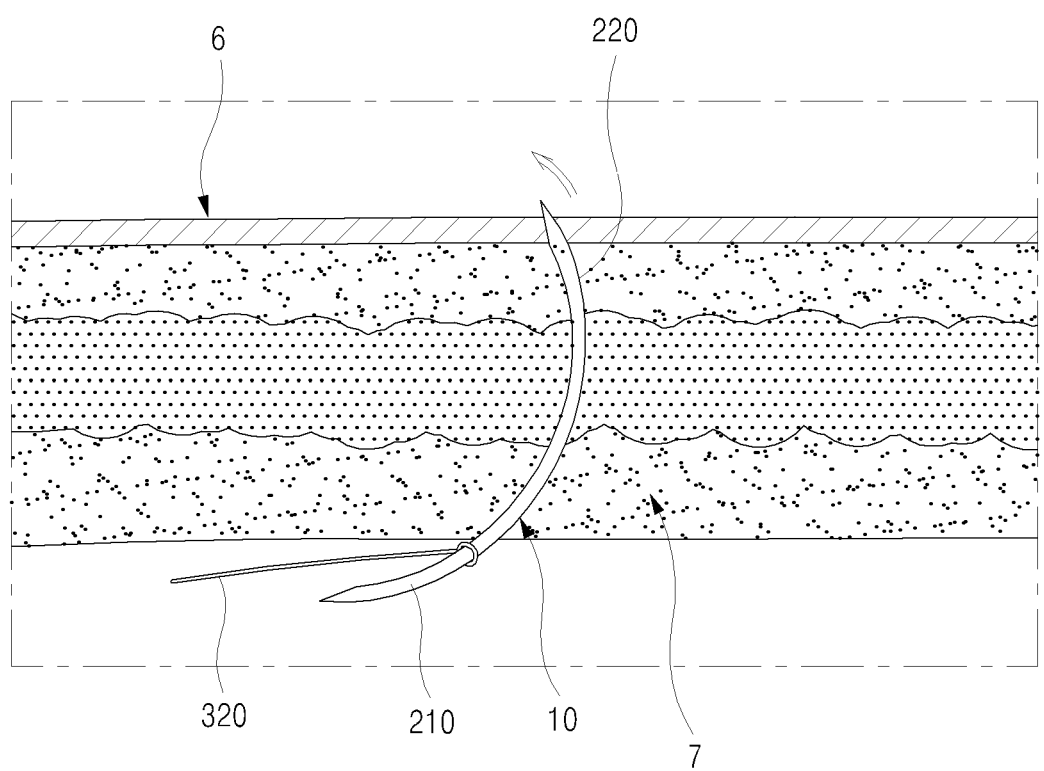
Figure 5C:
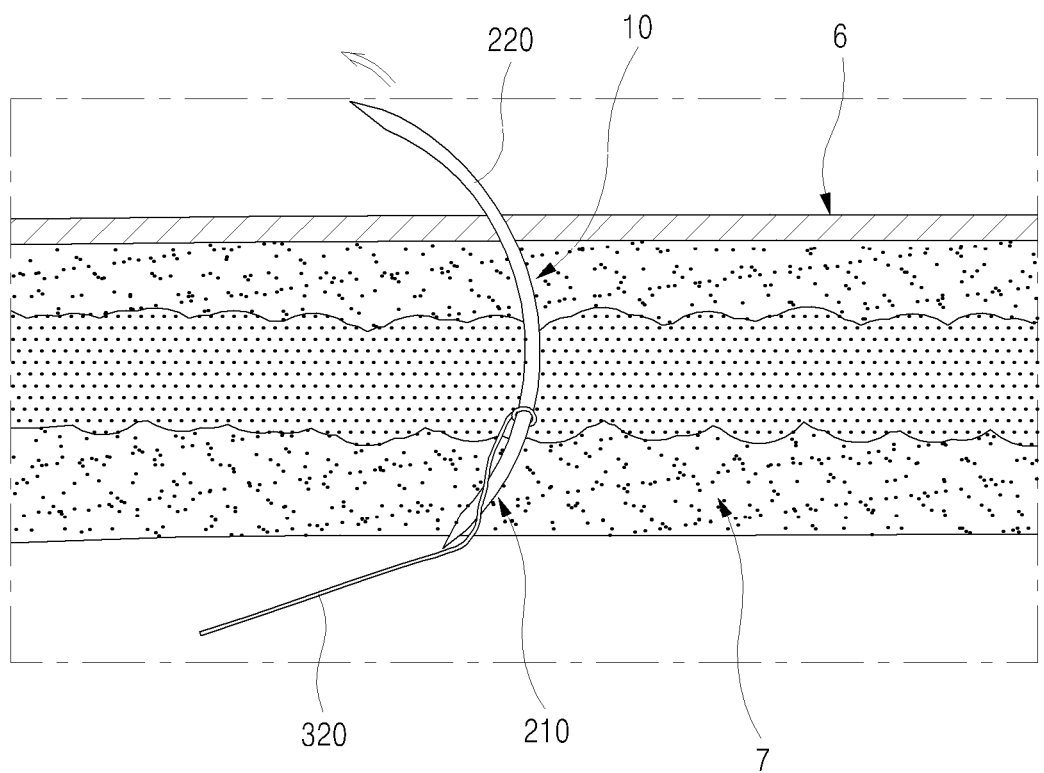
Figure 5D:
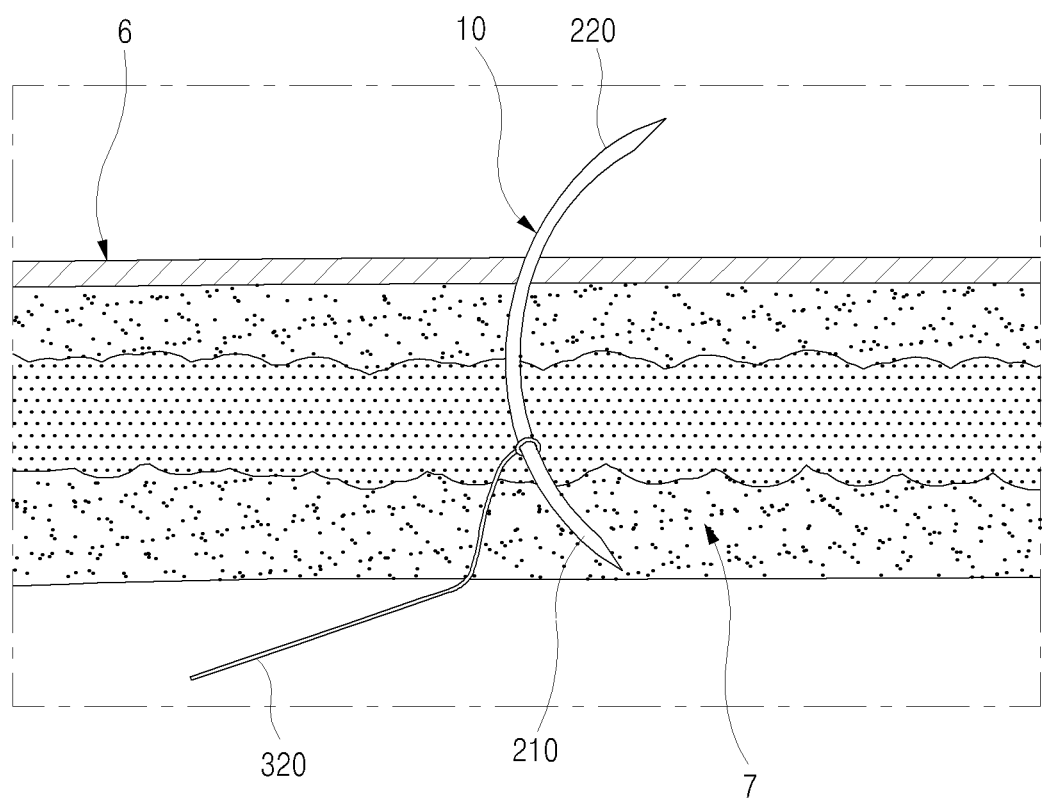
Figure 5E:
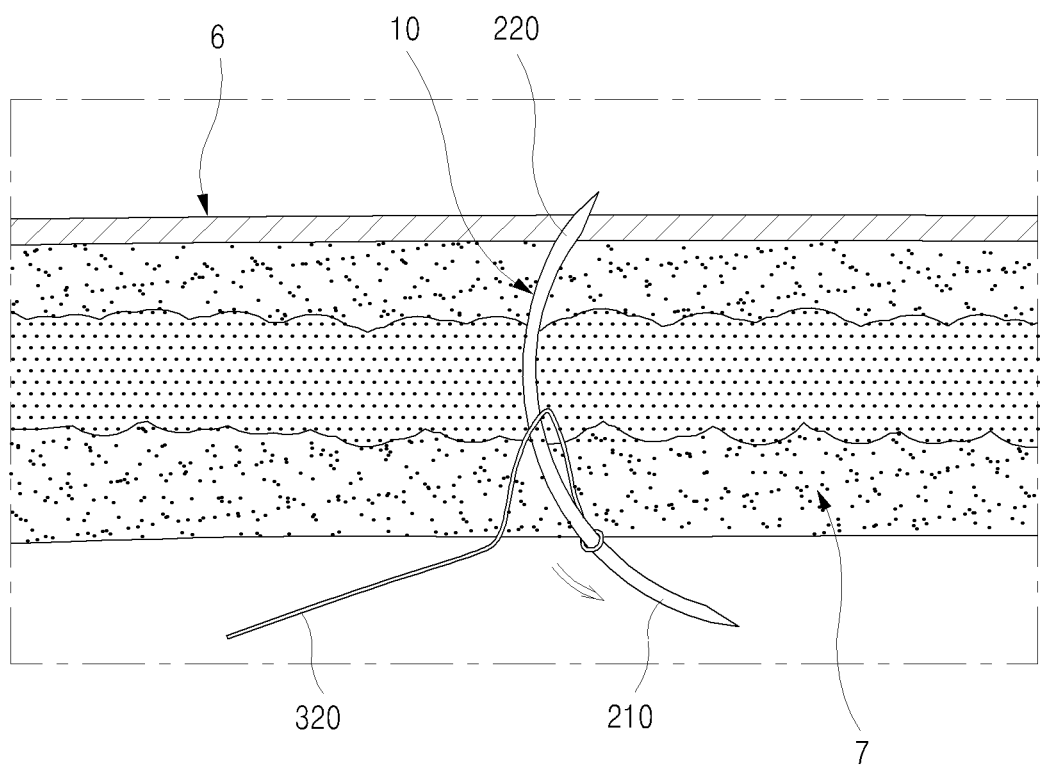
Figure 5F:
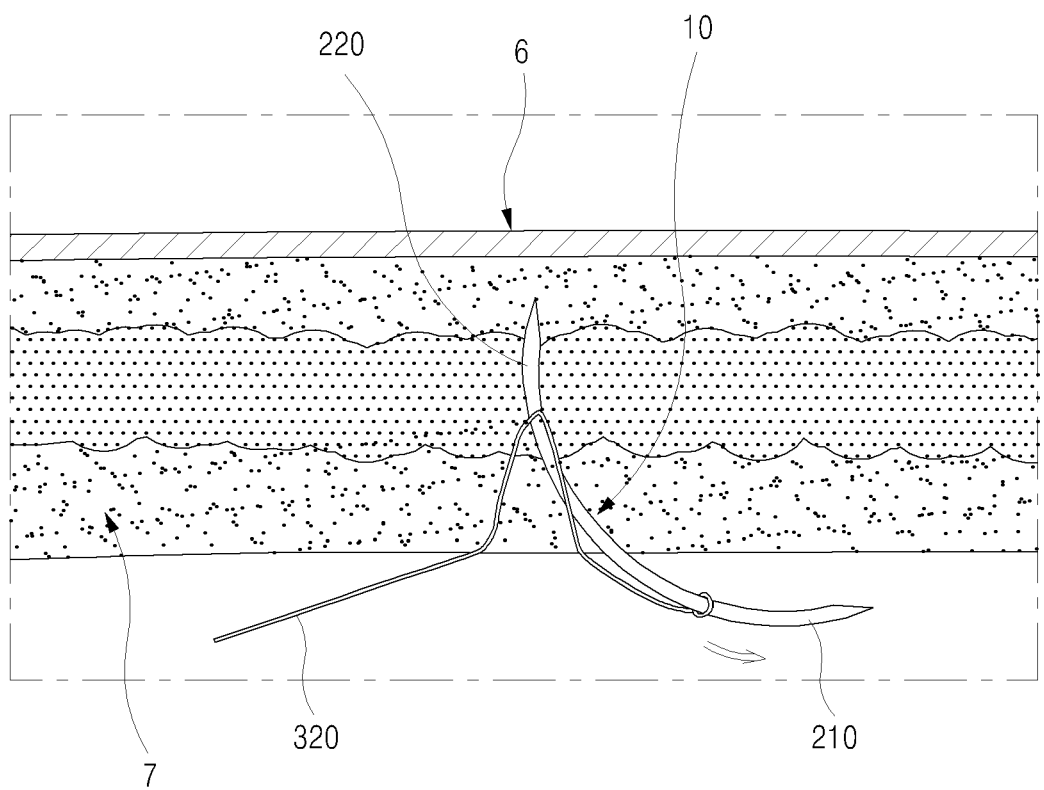

This procedure will be described below in more detail. The other needle side 220 of the needle instrument 10 is penetrated into the subcutaneous tissue 7 as illustrated in FIGS. 5A and 5B, so that the other needle side 220 is pulled out from the skin 6 as illustrated in FIG. 5C. Thereafter, if one needle side 210 is completely embedded into the subcutaneous tissue 7, the direction of the needle instrument 10 is changed at the outside as illustrated in FIG. 5D. Then, if the needle instrument 10 is pushed inwards and pulled out to the inside as illustrated in FIG. 5E, the thread 320 is caught by the subcutaneous tissue 7 as illustrated in FIG. 5F.

Subsequently, a part of the eye bag 4 is pulled downwards and relocated in the sunken lacrimal groove 5, and then the thread 320 is knotted, so that the relocated eye bag 4 is fixed by the thread 320 that is caught in the subcutaneous tissue 7. As a result, the internal fixing procedure of the eye bag is easily performed, and the eye bag is relocated at a sufficient lower position in the lacrimal groove, so that the effect of treatment is improved and a fixing force is excellent. Therefore, it is unnecessary to relocate the eye bag again.

Figure 6:
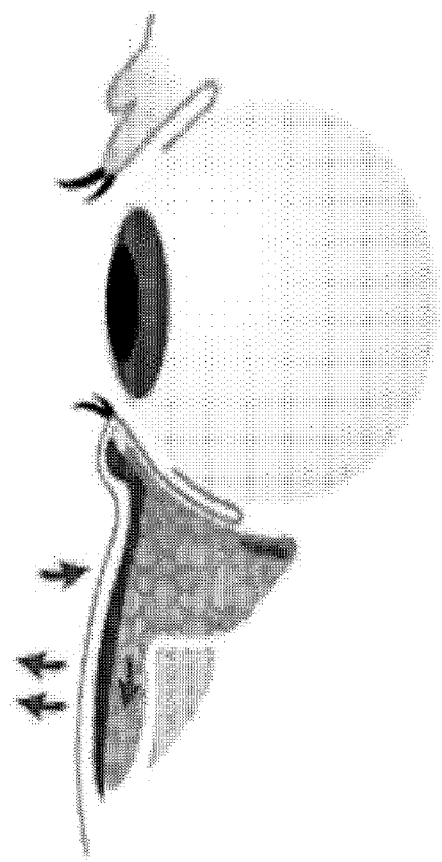
FIG. 6 is a view illustrating the result obtained after the operation of relocating the eye bag using the needle instrument according to the embodiment of the present invention is performed.

As such, if an operation is completed using the needle instrument 10 according to the present invention, as illustrated in FIG. 6, a dark circle is avoided and the eye bag is relocated. Thus, volume under the eye is restored over a sufficient area from the sunken lacrimal groove under the eye to the cheek and a natural baby face is achieved.

While the invention has been shown and described with reference to exemplary embodiments thereof, it will be understood by those skilled in the art that various changes in form and details may be made therein without departing from the spirit and scope of the invention as defined by the appended claims. Therefore, it is to be understood that the scope of the invention is not limited to the above-described embodiments, and all changes that fall within meets and bounds of the claims, or equivalence of such meets and bounds are intended to be embraced by the claims.

As described above, the present invention provides a needle instrument for an eye-bag relocating operation, which minimizes the incision of the conjunctiva inside the eye, reduces a scar in conjunctiva, facilitates an internal fixing procedure, and allows an eye bag to be relocated at a sufficient lower position in a lacrimal groove, so that the effect of treatment is improved and robust internal fixing is achieved, and consequently it is unnecessary to relocate the eye bag again, and a damage to skin and a dimple phenomenon where a skin surface is rugged after a surgical procedure may be prevented.

The invention claimed is:

1. A needle instrument for an eye-bag relocating operation, which is used to fix an eye bag relocated at a lower position in a lacrimal groove during the eye-bag relocating operation and has an arc shape, the needle instrument comprising:
    a body having a rectangular cross-section, and configured to be grabbed by a needle holder during the operation, the body including a first end and a second end;
    a first needle side and a second needle side respectively connected to the first end and the second end of the body, the first and second needle sides being tapered, and including round tips, wherein the first needle side tip is duller than the second needle side tip; and
    a thread pressing and coupling portion provided on the first end of the body, and disposed at a position that corresponds to ⅕ to ⅙ of an entire length from an end of the first needle tip and is spaced apart from the first end of the body by 0.5 to 1 mm, wherein, a through hole is disposed through the thread pressing and coupling portion and configured to be connected to a thread, and the first and second ends of the body are configured to be pressed by a press machine to attach the thread thereto.

2. The needle instrument of claim 1, wherein the body has a rounded edge.

3. A method of relocating the eye-bag using the needle instrument of claim 1, wherein, in a state where the needle instrument is inserted down through an incised conjunctiva inside an eye and the needle instrument is connected with the eye bag using the thread, after the second needle passes through skin tissue of the lacrimal groove to be exposed to an outside, the needle instrument is moved or rotated and the needle instrument is pulled out from the skin tissue starting from the first needle, so that the thread is caught in the skin tissue and a part of the eye bag is pulled downwards to be relocated in the lacrimal groove, and then the thread is knotted, so that the relocated eye bag is fixed by the thread caught in the skin tissue.

4. A needle instrument for an eye-bag relocating operation, which is used to fix an eye bag relocated at a lower position in a lacrimal groove during the eye-bag relocating operation and has an arc shape, the needle instrument comprising:
    a body having a rectangular cross-section, and configured to be grabbed by a needle holder during the operation, the body including a first end and a second end;
    a first needle side and a second needle side respectively connected to the first and second ends of the body, the first and second needle sides being tapered, wherein the first needle side comprises a round tip and the second needle side comprises a tip that is cut in a triangular shape; and
    a thread pressing and coupling portion provided on the first end of the body, and disposed at a position that corresponds to ⅕ to ⅙ of an entire length from an end of the first needle tip and is spaced apart from the first end of the body by 0.5 to 1 mm, wherein, a through hole is disposed through the thread pressing and coupling portion and configured to be connected to a thread, and the first and second ends of the body are configured to be pressed by a press machine to attach the thread thereto.

5. The needle instrument of claim 4, wherein the body has a rounded edge.

* * * * *